(12) United States Patent
Miller et al.

(10) Patent No.: US 8,507,555 B2
(45) Date of Patent: Aug. 13, 2013

(54) NON-TOXIC ANTI-CANCER DRUG COMBINING ASCORBATE, MAGNESIUM AND A NAPHTHOQUINONE

(75) Inventors: Thomas M. Miller, El Cajon, CA (US); James M. Jamison, Stow, OH (US)

(73) Assignee: Summa Health System, Akron, OH (US)

( * ) Notice: Subject to any disclaimer, the term of this patent is extended or adjusted under 35 U.S.C. 154(b) by 779 days.

(21) Appl. No.: 12/305,182

(22) PCT Filed: Jun. 15, 2007

(86) PCT No.: PCT/US2007/071361
§ 371 (c)(1),
(2), (4) Date: Sep. 18, 2009

(87) PCT Pub. No.: WO2007/147128
PCT Pub. Date: Dec. 21, 2007

(65) Prior Publication Data
US 2010/0056625 A1 Mar. 4, 2010

Related U.S. Application Data

(60) Provisional application No. 60/814,061, filed on Jun. 16, 2006.

(51) Int. Cl.
*A01N 43/08* (2006.01)
*A01N 35/00* (2006.01)
*A61K 31/34* (2006.01)

(52) U.S. Cl.
USPC .......................................... 514/474; 514/681

(58) Field of Classification Search
USPC .................................. 514/474, 681
See application file for complete search history.

(56) References Cited

U.S. PATENT DOCUMENTS

| 6,451,341 B1 * | 9/2002 | Slaga et al. ............... 424/468 |
| 2003/0073738 A1 | 4/2003 | Gilloteaux et al. |
| 2005/0123628 A1 | 6/2005 | Zabrecky |
| 2005/0261367 A1 | 11/2005 | Murad |
| 2006/0275504 A1 * | 12/2006 | Chen ........................... 424/623 |

FOREIGN PATENT DOCUMENTS

| WO | 98/15614 | 4/1998 |
| WO | 03057201 A2 | 7/2003 |

OTHER PUBLICATIONS

U.S. Appl. No. 13/384,574, filed Jan. 2012, Jamison et al.*
Casciari, J.J. et al. (2001). Cytotoxicity of ascorbate, lipoic acid, and other antioxidants in hollow fibre in vitro tumours. Brit. J. Cancer 84:1544-1550.
Tardy, C et al. (2006). Lysosomes and lysosomal proteins in cancer cell death (new players of an old struggle). Biochim Biophys. Acta 1765:101-125.
Gruenwald et al., "Safety and Tolerance of Ester-C® Compared With Regular Ascorbic Acid", Advances in Natural Therapy, 23(1):171-178, Jan./Feb. 2006.
Roomi et al., "In Vivo Antitumor Effect of Ascorbic Acid, Lysine, Proline and Green Tea Extract on Human Prostate Cancer PC-3 Xenografts in Nude Mice: Evaluation of Tumor Growth and Immunohistochemistry" 19: 179-184, 2005.
Roomi et al., "Antitumor effect of nutrient synergy on human osteosarcoma cells U-20S, MNNG-HOS and Ewing's sarcoma SK-ES.1" Oncology Reports, 13: 253-257, 2005.
Extended European Search Report (Dec. 29, 2011).
EPO Examination Report (Mar. 26, 2013).

* cited by examiner

*Primary Examiner* — Kara R McMillian
(74) *Attorney, Agent, or Firm* — Browdy and Neimark, PLLC

(57) ABSTRACT

Compositions comprising combinations of magnesium ascorbate (magnesium Vitamin C of "MgVC$_2$") and Vitamin K3 or (VK3) or a quinone and semiquinone analogue of VK3, are used in methods for killing or inhibiting the growth of tumor or cancer cells or preneoplastic cells in a subject, or for treating cancer in a subject in need of such treatment.

14 Claims, 1 Drawing Sheet

NaVC/VK3          MgVC$_2$/VK3
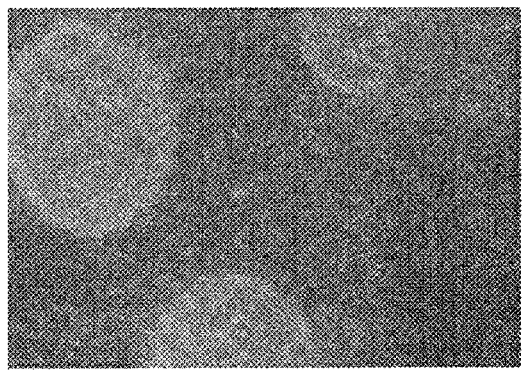 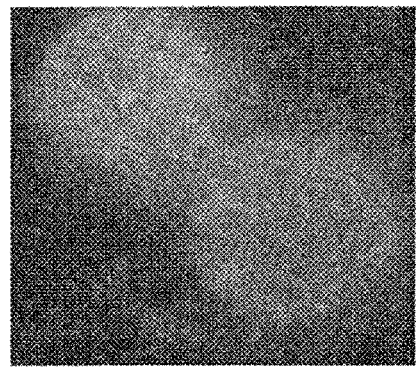
Fig. 1A          Fig. 1B
NaVC/VK3          MgVC$_2$/VK3
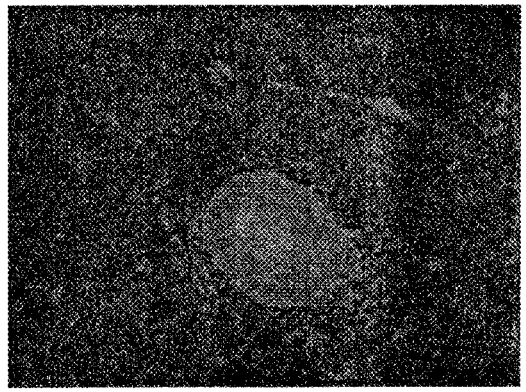 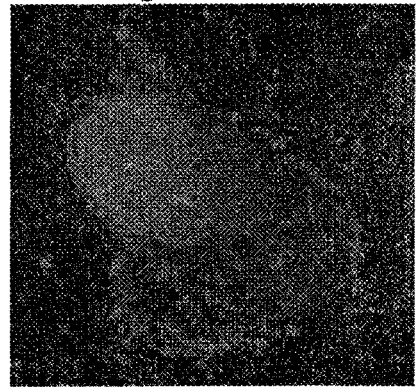
Fig. 2A          Fig. 2B
NaVC/VK3          MgVC$_2$/VK3
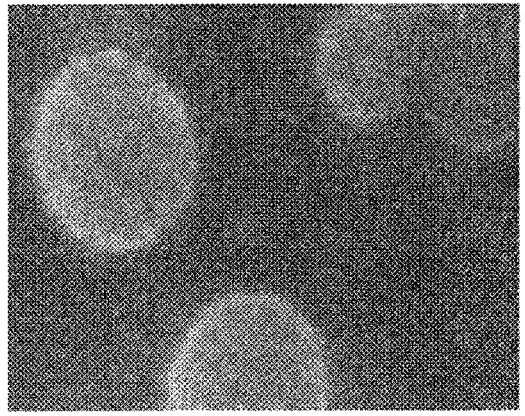 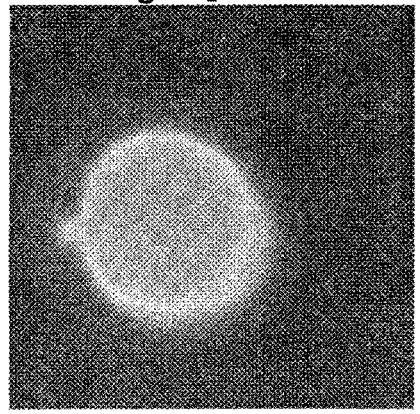
Fig. 3A          Fig. 3B

NON-TOXIC ANTI-CANCER DRUG COMBINING ASCORBATE, MAGNESIUM AND A NAPHTHOQUINONE

BACKGROUND OF THE INVENTION

1. Field of Invention

This invention in the field of biochemistry and medicine is directed to the prevention and treatment of human cancer by administration of a combination of magnesium ascorbate (magnesium Vitamin C or "MgVC$_2$") and the naphthoquinone Vitamin K3 (VK3) or a quinone and semiquinone analogue of VK3.

2. Description of the Background Art

In 1996, 554,740 Americans died from cancer. Ten years later, the National Cancer Institute estimates that 570,280 Americans will die of cancer in 2006.

Existing cancer treatment technologies are deficient. The present invention may prevent cancer and, when used in conjunction with traditional cancer therapies, it will improve the quality and the duration of life of cancer patients.

Much attention has focused on the role of vitamins in cancer prevention and treatment. Sodium ascorbate, also known as Vitamin C (VC), may act as an adjunct in improving responses to various types of cancer therapies. For example, VC potentiates the growth inhibitory effect of certain agents and increases the cytotoxicity of others. It is believed that VC may even reverse malignant cell transformation.

Vitamin K3 (chemical name: 2-methyl-1,4-naphthoquinone) is also believed to contribute to anti-cancer effects. The combination of Vitamin C and Vitamin K3 has been studied as a possible potentiating therapeutic modality for conventional chemotherapy. See, for example, U.S. Patent Publication 2003/0073738 (by one of the present inventors, Jamison, and colleagues).

A number of publications from the laboratory of H. Taper described studies of VC and VK3 in the context of cancer therapy. Taper H S et al., 1987, *Int J Cancer.* 40:575-9, disclosed intraperitoneal (i.p.) injection of mice with 1 g/Kg VC and 10 mg/Kg VK3 before or after a single treatment of several cytotoxic drugs.

Noto V et al., *Cancer* 1989, 63:901-6 discloses that (a) in vitro, addition of VC or VK3 at high concentrations inhibited the growth of several tumor cell lines (b) the addition of both compounds simultaneously appeared to have a synergistic effect in inhibiting cell growth (at markedly lower, nontoxic concentrations vs. each compound alone), and (c) the in vitro effect was completely suppressed by the addition of catalase to the culture medium containing the two vitamins. The authors concluded that excessive production of hydrogen peroxide was the responsible mechanism. However, it is likely that the in vitro results described in this document were explained by the fact that ascorbic acid, and many polyphenolic compounds generate H$_2$O$_2$ by interacting with components of the cell culture medium rather than by reactions with and in the cells themselves. See, for example, Halliwell B. et al., (2000) "Hydrogen peroxide. Ubiquitous in cell culture and in vivo?" *IUBMB Life* 50:251-257 and Clement, M. V. et al., (2001)

Taper H S et al., *Anticancer Res.* 1992, 12:1651-4, disclosed that i.p. treatment of mice with VC and VK3 sensitized tumors to the action of vincristine (Oncovin®). De Loecker W et al., *Anticancer Res.* 1993, 13:103-6, reported results of additional in vitro studies involving simultaneous exposure to VC and VK3. Taper H S et al., 1996, *Anticancer Res.* 16:499-503, discussed treatment of cancer with a VC/VK3 combination in conjunction with radiotherapy There remains a need in the art for improved methods of cancer treatment, including the enhancement of the efficacy of conventional treatment.

SUMMARY OF THE INVENTION

Certain Terms and Abbreviations Used Herein are Described in More Detail in the "Description of Preferred Embodiments" Section Below The present invention is directed to a novel composition (combination) and formulation and its use to prevent and treat cancer, either alone or in conjunction with traditional cancer therapies.

The invention is based on the unexpected discovery that in a combination drug, the substitution of magnesium ascorbate for sodium ascorbate in combination with Vitamin K3, results in more rapid and efficient killing of the cancer cells while maintaining a lower toxicity profile to normal cells. This new composition has been demonstrated to exhibit tumor-selective activity against human tumors.

The present invention was made as a consequence of studies investigating a new anti-cancer pharmacologic treatment (U.S. Patent Application Ser. Nos. 60/295,025 and 10/160, 152 and corresponding publication U.S. 2003/0073738). During phase I/II clinical studies of sodium L-ascorbate (also referred to herein as Vitamin C or VC), and 2-methyl-1,4-naphthoquinone also known as menadione sodium bisulfite and vitamin K3, abbreviated VK3) induced Gastrointestinal Esophageal Reflux Disease Symptoms (GERDS) in a significant number of study participants. To lessen symptoms, patients were instructed to take the medication with meals. However, it was not convenient to couple the drug dosing, at a frequency of up to 10 times per day, with a meal schedules. GERDS made the subjects uncomfortable and raised issues of noncompliance.

Reactivation of endogenous endonucleases is thought to be among the pleiotropic effects of treatment with sodium ascorbate and VK3. Optimal DNase I activity requires an alkaline pH and the presence of the divalent cations ($Ca^{2+}$ and/or $Mg^{2+}$). Since $Mg^{2+}$ buffers at alkaline pH, this cation was expected to ameliorate the acidic effects of sodium ascorbate, while reactivating DNase I (an important anti-neoplastic mechanism). Accordingly, the inventors evaluated the effect of using $Mg^{2+}$ in place of sodium as the ascorbate counterion in an effort to overcome the problem of GERDS.

The magnitude of the positive results in the selective cytotoxicity towards tumor cells and the activation of DNase I and II, described herein, were surprising and provided a basis for major clinical benefit for the novel combination.

The present invention is directed to a method of treating a patient having cancer by administering a combination of MgVC$_2$ and VK3 or an active quinone or semiquinone analogue thereof. This combination is also used as a supplement to conventional cancer therapy, wherein the combination is administered before and/or during, and/or following the administration of conventional cancer therapeutic agents or modalities such as radiotherapy and chemotherapy. The present invention is directed to methods of preparation of oral, intranasal, and intravenous formulations of the MgVC$_2$/VK3 combination.

The method of inhibiting the growth of a tumor or cancer that is sensitive to the effects of a MgVC$_2$/quinone combination (e.g., VK3 or an active quinone or semiquinone analogue thereof) comprises administering to a host in need of such treatment a combination of MgVC$_3$ and a VK3 or analogue in amounts synergistically effective to inhibit tumor growth.

The present invention includes a method of inhibiting metastasis of cancer cells sensitive to the effects of a vitamin C/quinone combination which comprises administering to a host in need of such inhibiting, a combination of $MgVC_2$ and a naphthoquinone, preferably VK3 or an active quinone or semiquinone analogue thereof, administered in an amount synergistically effective to kill cancer cells, prevent and/or inhibit tumor growth and development and inhibit tumor metastasis.

In addition to VK3, biologically active analogues that are either (a) quinones, such as benzoquinones, naphthoquinones, or anthraquinones, or (b) semiquinones may be substituted.

More specifically, the present invention is directed to a method of killing or inhibiting the growth of tumor or cancer cells in a subject in need thereof, comprising, administering to the subject an effective amount of a composition comprising, or consisting essentially of, a combination of magnesium ascorbate ($MgVC_2$) and Vitamin K3 (VK3) or an active quinone or semiquinone analogue thereof, more preferably VK3, in an amount effective to kill or inhibit the growth of the tumor or cancer cells. The method also kills or inhibits growth of cells of a precancerous lesion and prevents development of cancer from a precancerous state.

Also provided is a method for treating cancer in a subject in need of such treatment, the method comprising administering to the subject an effective amount of a composition comprising, or consisting essentially of, a combination of $MgVC_2$ and VK3 or an active quinone or semiquinone analogue thereof, more preferably VK3, in an amount effective to kill or inhibit the growth of the tumor or cancer cells.

In the above method, the ratio of $MgVC_2$ to VK3 or to its quinone or semiquinone analogue is preferably in the range of between about 50:1 and about 500:1, more preferably between about 100:1 and about 200:1, for example, about 100:1.

In the above method the amount of $MgVC_2$ administered orally to the subject per day is preferably between about 15 mg and 1 g per kg body weight, and the amount of VK3 or the analogue administered per day is preferably between about 30 µg and about 20 mg per kg body weight The above VK3, or quinone or semiquinone analogue may be in bisulfite form. A preferred active quinone analogue of VK3 is benzoquinone.

In the foregoing method, the administering is preferably oral, intranasal, intravenous or intraperitoneal, more preferably oral.

In the present method the administering is preferably oral, intranasal, intravenous or intraperitoneal results in the killing of cells of solid tumors or cancers, and hematological malignancies.

Preferably, cells being killed or inhibited are, for example, breast cancer cells, colon cancer cells, prostate cancer cells, lymphoma cells, leukemia cells, lung cancer cells, head or neck cancer cells, brain tumor cells, ovarian cancer cells, liver cancer cells, neuroblastoma cells, medulloblastoma cells, squamous cell carcinoma cells, carcinoma in situ cells or basal cell carcinoma cells. The cells being killed or inhibited may be cancer cells that developed from an identifiable or recognized precancerous lesion or they may be cells of the precancerous lesion, for example actinic keratosis. Treatment that results in the killing or inhibition of these precancerous cells will treat the actinic keratosis and/or inhibit the development of squamous cell carcinoma from the actinic keratosis.

Preferably, the tumor or cancer being treated in the subject is, accordingly, breast cancer, colon cancer, prostate cancer, lymphoma, leukemia, lung cancer, head or neck cancer, a brain tumor, ovarian cancer, liver cancer, neuroblastoma, medulloblastoma, squamous cell carcinoma, carcinoma in situ or basal cell carcinoma.

The administering of the composition noted above preferably results in:
(a) a partial response, characterized as at least a 50% decrease in the sum of the products of maximal perpendicular diameters of all measurable tumor lesions without evidence of new lesions or progression of any preexisting lesions, or
(b) a complete response characterized as the disappearance of all evidence of the cancer or tumor for at least one month.

In another embodiment, the invention is directed to a composition useful in the above method of killing or inhibiting the growth of tumor or cancer cells or for treating cancer in a subject in need thereof, which composition comprises, or consists essentially of, a combination of $MgVC_2$ and Vitamin K3 or an active quinone or semiquinone analogue thereof, most preferably VK3.

In the composition, the ratio of $MgVC_2$ to VK3 or to its quinone or semiquinone analogue is preferably in the range of between about 50:1 and about 500:1, more preferably between about 100:1 and about 200:1

Preferably, in the composition, the VK3, or quinone or semiquinone analogue is in bisulfite form. A preferred quinone analogue of VK3 is benzoquinone.

Also provided is a pharmaceutical composition comprising the above composition and a pharmaceutically acceptable carrier or excipient. The pharmaceutical composition is preferably formulated as a capsule for oral administration. The invention includes a kit comprising a plurality of the capsules, and, optionally, directions for use of the capsules.

The invention provides a dosing regimen for a combination of $MgVC_2$ and a quinone such as VK3 for treating a host in conjunction with a conventional cancer treatment protocol. The dosing regimen comprises
(1) a first phase in which a first amount of the combination is administered to the host daily from an initial treatment day up until two days prior to initiation of the conventional treatment;
(2) a second phase in which a second amount of the combination is administered for two days prior to initiation of the conventional treatment;
(3) a third phase in which a third amount of the combination is administered on the same day as the conventional treatment;
(4) a fourth phase in which a fourth amount of the combination is administered on the day following the conventional treatment.

Also provided is a method for monitoring the effectiveness of a the present cancer treatment which is based on measuring a serum alkaline DNase activity of the patient before, during, and after administration of the present composition and/or conventional anti-cancer agents.

Also included is a kit comprising a plurality of capsules, each capsule comprising a combination of $MgVC_2$ and VK3 or an active quinone or semiquinone analogue thereof, and, optionally, directions for use of the capsules.

Below is a list of advantages of the present invention, related to the importance of $Mg^{2+}$ in normal cell function, over related formulations of the prior art (primarily over the combination of VC/VK3.
(a) more rapid killing of a larger number of cancer cells
(b) improved targeting due to the fact that $Mg^{2+}$ is an intracellular cation; imaging demonstrates that cell targeting and anticancer effects are improved.
(c) improved re-expression of DNases in neoplastic cells (d) enhanced safety because $Mg^{2+}$ protects normal healthy cells due to its behavior as a free radical scavenger and catalyst of various normal cellular functions (see results of MTT assays of fibroblasts in Examples (e) improved effects on energy production, transport and bioavailability. This is related to the fact that $Mg^{2+}$ is important to ATP production, transport and utilization. Sodium plays no appreciable role in intracellular bioenergetics. Use of $Mg^{2+}$ in the formulation would play a role in cellular bioenergetics that is important for anti-neoplastic activity.

(f) better side effect profile, particularly with respect to GERDS. Mg-stabilized ascorbate permits higher doses without induction of GERDS.

(g) improved compliance in oral administration as a result of the improved drug chemistry which would reduce capsule size, also enhancing patient compliance.

BRIEF DESCRIPTION OF THE DRAWINGS

FIGS. 1A-1B show the effect on nuclear DNase I activity of treatment of human bladder carcinoma cells (T24) with the earlier described Combination A—NaVC/VK3 (FIG. 1A) and Combination B, which is the $MgVC_2$/VK3 formulation of the present invention (FIG. 1B). The concentrations of the formulations were as follows: 125 μM NaVC/1.25 μM $VK_3$ and 62.5 μM $MgVC_2$/1.25 μM $VK_3$. In the presence of NaVC/VK3, nuclear DNase I distribution remained repressed (bound to actin). $MgVC_2$/VK3 resulted in a derepression distribution.

FIGS. 2A-2B show the effect on nuclear DNase II activity of treatment of T24 human bladder carcinoma cells of with NaVC/VK3 and $MgVC_2$/VK3 as described for FIGS. 1A/1B. The cell nucleic were stained with 4',6-diamidino-2-phenylindole (DAPI). The results indicate that in the presence of NaVC/VK3, DNase II remained repressed whereas $MgVC_2$/VK3 exposure resulted in derepression.

FIGS. 3A-3B show the effect on nuclear DNA distribution of treatment of T24 human bladder carcinoma cells of NaVC/VK3 and $MgVC_2$/VK3 as described for FIGS. 1A/1B. The results indicate that in the presence of NaVC/VK3, DNA distribution was normal whereas $MgVC_2$/VK3 resulted in redistribution of DNA to a condensed appearance.

DESCRIPTION OF THE PREFERRED EMBODIMENTS

Definitions and Abbreviations

VC—vitamin C, sodium ascorbate, also abbreviated as NaVC. The chemical structure is shown below

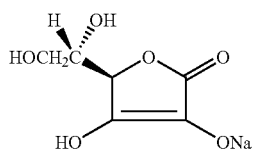

MGVC or $MgVC_2$—magnesium salt of ascorbate, or magnesium ascorbate; due to the divalency of the $Mg^{2+}$ ion, the compound has the stoichiometry of two ascorbate anions per $Mg^{2+}$ cation, which is better described by the "$MgVC_2$" designation. Note that the subscripted 2 is used to indicate the number of molecules of ascorbate, not a number of atoms (as is the usual meaning in chemical formulas). The use of a capital "C" in this abbreviated formula is not intended to mean carbon—although C does represent carbon in some "standard" chemical formulations used herein.

VK3—Vitamin K3 or menadione is a polycyclic aromatic ketone, based on 1,4-naphthoquinone, with a 2-methyl substituent. Its chemical name is 2-methyl-1,4-naphthoquinone or 2-methylnaphthalene-1,4-dione, and its the chemical formula is $C_{11}H_8O_2$, molecular mass 172.18. The chemical structure is shown below

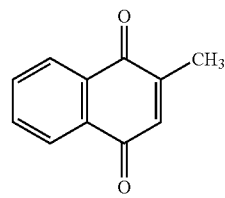

Menadione is also a vitamin precursor of $K_2$ which utilizes alkylation in the liver to yield menaquinones (MK-n, n=1-13; $K_2$ vitamers), and hence, may be classified as a provitamin. Vitamin K3 is more typically shown as "$K_3$" in the literature. However in this application, the subscripted 3 is not used to avoid confusion (because of the use of the subscripted 2 in the abbreviation $MgVC_2$ to indicate the number of molecules in the formulation.

The preferred form of VK3 in the present invention is the bisulfite form because it is water soluble, and does not accumulate in fat tissue of the subject. The chemical structure is shown below.

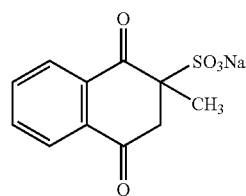

In various embodiments of the present invention, the preferred embodiment of VK3 can be replaced by any quinone or semiquinone analogue of VK3 that has similar biological activity, primarily in anti-cancer activity in combination with a VC formulation. Thus, it should be understood that in a formulation $MgVC_2$/VK3, the VK3 can be substituted with an equimolar amount of another such quinone or semiquinone. Benzoquinone is one example of a quinone with cancer-inhibiting activity (to several colon cancer lines growing in mice) In accordance with the present invention, a preferred quinone is Vitamin $K_3$.

VC/VK3, NaVC:VK3, $MgVC_2$/VK3, $MgVC_2$:VK3—These abbreviations, using a slash or colon, represent combinations of a form of Vitamin C with a form of Vitamin K3.

GERDS—Gastrointestinal Esophageal Reflux Disease Symptoms

A "neoplastic" cell exhibits uncontrolled proliferation. Generally, progeny of a neoplastic cell are also neoplastic and do not undergo terminal differentiation in vivo in response to physiological signals. Neoplastic cells include cells that are also described as cancer cells, cancerous cells and transformed cells. Neoplastic cells may occur as single, isolated cells in the body or aggregated, either homogeneously (with other neoplastic cells) or heterogeneously, with other cell types, as in a tumor or other collection of cells. A "tumor" is a collection of cells (neoplastic or otherwise) in which at least some of the cells are in physical contact with one another, typically by sharing a common extracellular matrix.

"Autoschizic cell death" or "autoschizis" is a more recently recognized type of cell death distinct from necrosis and apoptosis that is considered to be a form of necrosis characterized by exaggerated membrane damage and progressive loss of organelle-free cytoplasm through a series of self-excisions.

"Synergistic effective amount" is an amount of $MgVC_2$/VK3 that is effective to produce positive results of the combination compared to the results achieved by either component alone in the treatment of a cancer patient.

The present invention is directed to cancer treatment methods that include "monotherapy" with $MgVC_2$/quinone, $MgVC_2$/hydroquinone, most preferably $MgVC_2$/VK3 to attenuate, retard, inhibit, decrease, impede, or reverse, etc., tumor development and growth. The ability of the present compositions and methods act in a preventative manner results in substantially reduced size of tumor, and even its elimination, thereby preventing, attenuating or reversing any pathological effects of the tumor or cancer on the patient.

Also intended is the use of the present formulations in conjunction with other conventional cancer treatments, including chemotherapy, radiotherapy, and biotherapy. This invention represents an improvement over previous discoveries that the VC/VK3 combination can exerts antitumor and antimetastatic effects mediated by any of a number of mechanisms which may include cell cycle blockade, modulation of signal transduction pathways, potentiation of the immune system, direct induction of autoschizic cell death When used as a supplemental treatment, the method of the present invention, because of its nontoxic nature, can be initiated before the start of conventional treatment, continued during intervals between subsequent recurring rounds of conventional therapy, and may be continued after cessation of conventional therapy.

Treatment of cancer, a tumor, a premalignant disease or a hyperproliferative disorder by the present compositions includes the killing, inhibiting or slowing the growth of the relevant target cells, or inhibiting the increase in size of a tumor or cancerous growth. This includes reducing cell numbers, or preventing metastasis. "Treatment" as used herein is not meant to imply or require total cure or disappearance of cancer or a growing tumor. "Treatment" or "treating" is also intended to include prophylaxis, i.e., the prevention of development of a tumor or cancer, either a primary tumor, or more commonly a metastatic tumor or a recurrent tumor at the same or a different site from the primary tumor.

Malignant and metastatic diseases and conditions (tumors and cancer) which can be treated in accordance with the present invention include, but are not limited to, solid tumors, e.g., carcinomas, sarcomas, lymphomas and other malignant or nonmalignant tumors such as those listed below. For a review of such disorders, see any textbook of clinical oncology, e.g., DeVita, V T et al., (eds), *Cancer: Principles and Practice of Oncology*, 7$^{th}$ Edition, Lippincott Williams & Wilkins; 2004).

The terms "cancer," "carcinoma," and "cancerous" when used herein refer to or describe the physiological condition, preferably in a mammalian subject, that is typically characterized by unregulated, neoplastic cell growth.

Examples of types of cancers that are successfully treated by the present compositions and methods are presented in the list below and in Table 1, which is not intended to be limiting. Thus the present invention is directed to the treatment of pancreatic carcinomas, renal cell carcinomas, small cell lung carcinoma, non-small cell lung carcinoma, prostatic carcinoma, bladder carcinoma, colorectal carcinomas, breast, ovarian, endometrial and cervical cancers, gastric adenocarcinoma, primary hepatocellular carcinoma, genitourinary adenocarcinoma, thyroid adenoma and adenocarcinoma, melanoma, retinoblastoma, neuroblastoma, mycosis fungoides, pancreatic carcinoma, prostatic carcinoma, bladder carcinoma, myeloma, diffuse histiocytic and other lymphomas, Wilms' tumor, Hodgkin's disease, adrenal tumors (adrenocortical or adrenomedullary), osteogenic sarcoma, soft tissue sarcoma, Ewing's sarcoma, rhabdomyosarcoma and acute or chronic leukemias, islet cell cancer, cervical, testicular, adrenocortical, or adrenomedullary cancers, choriocarcinoma, embryonal rhabdomyosarcoma, Kaposi's sarcoma, etc.

TABLE 1

| List of Cancers/Tumors |
|---|
| acoustic neuroma |
| adenocarcinoma |
| angiosarcoma |
| astrocytoma |
| basal cell carcinoma |
| bile duct carcinoma |
| bladder carcinoma |
| breast cancer |
| bronchogenic carcinoma |
| cervical cancer |
| chondrosarcoma |
| choriocarcinoma |
| colorectal carcinomas |
| craniopharyngioma |
| cystadenocarcinoma |
| embryonal carcinoma |
| endotheliosarcoma |
| ependymoma |
| esophageal carcinoma |
| Ewing's tumor |
| fibrosarcoma |
| gastric carcinoma |
| Glioma/glioblastoma |
| Head and neck cancers |
| Hemangioblastoma |
| Hepatocellular carcinoma |
| Hepatoma |
| Kaposi's sarcoma |
| leiomyosarcoma |
| liposarcoma |
| lung carcinoma |
| lymphangiosarcoma |
| lymphangioendotheliosarcoma |
| Lymphoma |
| Leukemia |
| medullary carcinoma |
| medulloblastoma |
| Melanoma |
| meningioma |
| mesothelioma |
| Multiple myeloma |
| Myxosarcoma |
| Nasopharyngeal carcinoma |
| Neuroblastoma |
| oligodendroglioma |
| osteogenic sarcoma |
| ovarian cancer |
| pancreatic cancer |
| papillary adenocarcinomas |
| pinealoma |
| prostate cancer |
| renal cell carcinoma |
| retinoblastoma |
| rhabdomyosarcoma |
| sebaceous gland carcinoma |
| seminoma |
| small cell lung carcinoma |

TABLE 1-continued

List of Cancers/Tumors squamous cell carcinoma
sweat gland carcinoma
synovioma
testicular tumor
Thyroid cancer
Wilms' tumor The methods and compositions of the present invention are also used to treat precancers and prevent their progression to cancer, as indicated above.

During cancer progression, distinctive lesions occur that persist for a time and that they have a set of characteristic properties that permit them to be detected, diagnosed, prevented, and treated. A recent publication (Berman, J et al, 2006, *Cancer Detec Prevent.* 30:387-94, incorporated by reference in its entirety) summarized results of a consensus conference held in 2004 sponsored by the National Cancer Institute to develop a newer definition of precancers. The participants developed a working definition for the precancers that clinicians and researchers can use to distinguish precancers from non-neoplastic changes and from other types of changes that might be encountered during "cancer progression." This definition modified and made more general an earlier definition that had been proposed for endometrial intraepithelial neoplasia (e.g., Mutter G L et al., In: Crum C P et al, eds. *Diagnostic gynecologic and obstetric pathology.* Philadelphia: Saunders, 2006). All of the following five criteria were considered to apply in defining precancer:

(1) Evidence exists that the precancer is associated with an increased risk of cancer.
(2) When a precancer progresses to cancer, the resulting cancer arises from cells within the precancer.
(3) A precancer is different from the normal tissue from which it arises.
(4) A precancer is different from the cancer into which it develops, although it has some, but not all, of the molecular and phenotypic properties that characterize the cancer.
(5) There is a method by which the precancer can be diagnosed.

These five criteria were considered to represent the minimal set of conditions, necessary and sufficient, for a lesion detected by any method to be considered a precancer. All of the criteria must apply concurrently. The different kinds of precancers may vary in every biologic feature except those specified in the definition (identifiable lesions that precede the development of cancer). It is notable that the definition has no required morphologic criteria. Most earlier definitions of precancers presumed specific morphologic features that permitted them to be recognized. The specific diagnostic criteria are not limiting, so that cytogenetic, molecular, and even behavioral (phenotypic) properties are considered. A number of issues remained open after this conference.

While a number of human cancers have an identifiable precancer (see Table 2 below) it is expected that information regarding putative nonepithelial precancers will emerge as new genomic, proteomic, and functional data are generated in these non-epithelial models. Although the best examples of precancers today are epithelial, the definition adopted above is sufficiently general and open ended to be applicable to non-epithelial precancers.

Precancers are not obligate lesions preceding cancers. For example, adenomas are precancerous lesions that may lead to the development of colorectal carcinoma. However, it is not known whether every colorectal carcinoma is preceded by an adenoma, or whether some cases of colorectal carcinoma arise ab initio from a single transformed cell that appeared within a population of normal cells, and which was not associated with an identifiable precancerous lesion. Obviously, the practical benefits of precancer detection and therapy are diminished when the interval between the appearance of a precancer and its progression to an invasive cancer is brief.

At the histological level, epithelial precancers are relatively easy to define and to diagnose. Most are characterized as foci of atypical cells confined within the normal anatomic boundary of the epithelial compartment (i.e., the basement membrane). Atypical cells that have penetrated the basement membrane are considered malignant because they are invasive. The term "intraepithelial neoplasia" describes these lesions and includes specific criteria for their diagnosis. Despite certain open issues, precancers have distinctive biological properties that serve to separate them from the cancers, even if there is no intraepithelial compartment that can be examined for invasion. Some of the general properties of precancers that would apply to non-epithelial and epithelial precancers are described below.

TABLE 2

Most frequently occurring cancers of man all have identifiable precancerous lesions*

| Identifiable Precancerous Lesion | → Cancer that develops |
|---|---|
| Actinic keratosis/squamous cell carcinoma in situ | → Squamous carcinoma of skin |
| Adenocarcinoma in situ of endocervix | → Invasive adenocarcinoma of endocervix |
| Atypical ductal dysplasia/carcinoma in situ | → Invasive ductal carcinoma of breast |
| Atypical endometrial hyperplasia | → Endometrioid adenocarcinoma |
| Barrett's esophagus/dysplasia | → Esophageal adenocarcinoma |
| Bronchial squamous dysplasia/carcinoma in situ | → Squamous cell carcinoma of the lung |
| Cervical intraepithelial neoplasia | → Cervical squamous carcinoma |
| Colorectal adenoma | → Colorectal carcinoma |
| Gallbladder dysplasia/carcinoma in situ | → Invasive carcinoma of the gallbladder |
| Gastric dysplasia/carcinoma in situ | → Gastric adenocarcinoma |
| In situ medullary thyroid carcinoma | → Medullary thyroid carcinoma |
| In situ melanoma | → Melanoma |
| Intratubular germ cell neoplasia | → Invasive germ cell neoplasms |
| Myelodysplastic syndrome | → Leukemia |
| Oral dysplastic leukoplakia | → Oral squamous carcinoma |
| Pancreatic intraepithelial neoplasia | → Pancreatic adenocarcinoma |
| Progressive transformation of germinal centers | → Hodgkin's disease |

TABLE 2-continued

Most frequently occurring cancers of man all have identifiable precancerous lesions*

| Identifiable Precancerous Lesion | → Cancer that develops |
|---|---|
| Prostatic intraepithelial neoplasia | → Prostatic adenocarcinoma |
| Urothelial carcinoma in situ | → Invasive urothelial carcinoma |

Henson D E et al., eds. Pathology of incipient neoplasia. 3rd ed. New York: Oxford University Press, 2001; Greenberg A K et al., 2002, Respir Res. 3: 20-30; Bostwick D G et al., 2004, High-grade prostatic intraepithelial neoplasia. Mod Pathol 17: 360-79.; Henson D E et al., In: Kelloff G et al., eds., Cancer chemoprevention strategies for cancer chemoprevention, vol. 2. Totowa, NJ: Humana Press, 2005: pp 69-96; Hruban R H et al., 2004, Am J Surg Pathol 28: 977-87.

Regression— not all precancers progress to cancer. The regression rate of all precancerous lesions of bronchial epithelium was found to be 54% in one study (Breuer R H et al., 2005, *Clin Cancer Res* 11:537-43) and was unrelated to various risk factors. In cervical intra-intraepithelial neoplasia, on the other hand, lack of progression or regression was directly related to the degree of cytologic atypia, mitotic activity, and type of human papillomavirus infection (Nasiell K et al., 1983, *Obstet Gyneco;* 61:609-14). Most in situ neuroblastomas do not evolve into clinically apparent tumors (Henson et al., 2001, supra). In some nonepithelial malignant tumors, regression may be common (Krikorian J G et al., 1980, *Cancer* 46:2093-9). For instance, clinical regression was reported in 30% of cases of untreated follicular lymphomas (Homing S J et al., 1984 *N Engl J Med* 311:1471-5). Regression has rarely been reported in testicular germ cell neoplasms, neuroblastoma, melanoma, and other invasive cancers (Simpson K et al., 2007, *Ann Diag Pathol* 11:97-102). Regardless of the method of detection the lesions designated as precancers are often members of a biologically heterogeneous group comprised of some lesions that progress to cancer and other lesions, usually the majority, that persist without developing into invasive cancer or that regress. At present, it is not possible to distinguish precancers that progress from those (of similar morphology) that do not progress or that regress.

Precancer Progression:

Even though it is difficult to distinguish precancers that progress from those that do not progress, on a practical level again, epithelial precancers that do progress usually show greater cytologic atypia, more mitotic activity, and more genetic abnormalities than those that persist or regress. If a proliferative lesion typically transforms, over time, into a more aggressive lesion with identifiable features of the malignant phenotype not observed in the original lesion, this would be another reason to suspect that the original lesion is a precancer. Examples of non-epithelial proliferative lesions that occasionally transform into a more aggressive and morphologically malignant tumor are shown in Table 3.

Multiplicity of Lesions:

Carcinogenic agents often produce multiple precancers in animal models. Over time, some of these develop into cancers (McDonnell T J et al., 1991, *Nature* 349:254-6; Solt D B et al., 1977, *Am J Pathol* 88:595-618; Kirkpatrick C J et al., 2000, *Am J Pathol* 156:1455-67). The occurrence of multiple precancers seems also to exist in humans. An individual with hundreds of actinic keratoses is more likely to have one or more squamous cell carcinomas than an individual with only a few keratoses. An individual with hundreds of nevi will likely have a smaller number of atypical nevi and a very small number of malignant melanomas. Colon adenomas that develop in familial adenomatous polyposis are often synchronous and multiple, but it is unusual to find patients with multiple colon carcinomas. When a proliferative lesion is multiple, it may well be a precancer. A number of human cancers are components of inherited neoplastic syndromes, such as MEN type IIa. Patients with this syndrome develop a precancerous lesion, known as C-cell hyperplasia or medullary thyroid carcinoma in situ (Albores-Saavedra J et al., 2001, *Endocr Pathol* 12:365-77). This precancerous lesion is often multicentric, nearly always bilateral, and can be detected by identification of the specific RET germline mutation. Other genetically determined syndromes are characterized by precancerous lesions that are multicentric and diagnosed preoperatively by genetic testing.

Chronologic Precedence:

Progression of precancers to cancer, if it occurs, takes place over time. Thus, for any given precancer, the average age of individuals in whom the precancer occurs should be younger than the average age of individuals in which the developed cancer occurs. The property of chronological precedence seems to be an inescapable truth. If populations were screened at regular intervals, and if there were methods to reliably detect precancers and cancers, it might be feasible to use epidemiologic data to determine the chronologic precedence of precancers. With few exceptions, this type of study has not been carried out.

TABLE 3

Examples of non-epithelial proliferative lesions that occasionally transform into a more aggressive and morphologically malignant tumor

| Lesion | → Malignant Tumor |
|---|---|
| Fibrous dysplasia | → Osteosarcoma |
| Neurofibroma | → Malignant peripheral nerve sheath tumor |
| Osteochondroma | → Chondrosarcoma of bone |
| Progressive transformation of germinal centers | → Lymphocyte-predominant Hodgkin's disease |

Pharmaceutical and Therapeutic Compositions and Their Administration

Preferred ratios of $MgVC_2$ to VK3 (or other quinone or semiquinone) for the present compositions of methods if from about 50:1 to abut 500:1. A more preferred range of ratios is 100:1 to 200:1. Most preferred is a ratio of 100:1.

The maximum dosage of the combination is limited by the dose of the quinone (typically VK3) as this family of molecules is believed to be toxic at higher concentrations. For oral administration, the dose of $MgVC_2$ may range from about 15 mg to about 1 g per Kg body weight per day. The dose range of the VK3 or a biologically active quinone or semiquinone analogue may range from about 30 µg to about 20 mg/Kg body weight/day.

For i.v. or i.p, administration, the dose of $MgVC_2$ is preferably in the range of may be is 500 mg to about 500 g/Kg/day. In a preferred embodiment, the dose is about 50-100 g/Kg/day.

The dose of the quinone, preferably VK3 is preferably in the range of about 1 mg to about 10 g/kg body weight/day. More preferred doses are in the rage of about 0.5 to about 2 g/kg/day.

The vitamin combination can be administered by any suitable manner or route, preferably e.g., orally, i.v. or i.p. The two vitamins can also be delivered by different routes, e.g., injection of VK3, and oral administration of MgVC$_2$. In a preferred embodiment, both oral and intravenous administration are utilized during the course of treatment.

The therapeutic dosage administered is an amount which is therapeutically effective in treating the target disease, preferably cancer, as is known or readily ascertainable by those skilled in the art. The dose is also dependent upon the age, health, and weight of the recipient, state or stage of the cancer, nature of concurrent treatment(s) if any, the frequency of treatment, and the nature of the effect desired. Effective doses or amounts can be determined in view of this disclosure by one of ordinary skill in the art by carrying out routine trials with appropriate controls. Comparison of the appropriate treatment groups to the controls will indicate whether a particular dosage is effective. An effective amount of the compound to treat a tumor or cancer is an amount sufficient to achieve a steady state concentration in vivo which results in treatment, healing, prevention, prophylaxis, amelioration, or reduction in the symptoms. In the art of tumor or cancer therapy, this preferably refers to a measurable reduction in a relevant parameter of disease such as attenuating or reversing growth of a primary or a metastatic tumor, reduction in tumor load, preventing or reducing recurrence or metastasis of a primary tumor, or a measurable prolongation of disease-free interval or of survival. For example, a reduction in tumor growth in 20% of patients is considered efficacious or effective. (See, for example, Frei III, E., "Clinical trials of antitumor agents: experimental design and timeline considerations," *Cancer J Sci Am.*, 1997, 3: 127-36.) However, an effect of this magnitude is not considered to be a minimal requirement for the dose to be effective in accordance with this invention. Therapeutic or treatment responses can be complete response (CR) or partial responses (PR). DeVita et al, supra). Table 4, below shows accepted definitions, established by the International Union Against Cancer:

TABLE 4

| RESPONSE | DEFINITION |
| --- | --- |
| Complete response (CR) | Disappearance of all evidence of disease |
| Partial response (PR) | >50% decrease in tumor burden; no new lesions; no progression of pre-existing lesions |
| Less than partial response (<PR) | 25-50% decrease in tumor size, stable for at least 1 month |
| Stable disease | <25% reduction in tumor size; no progression or new lesions |
| Progression | >25% increase in size of any one measured lesion or appearance of new lesions despite stabilization or response of disease in other measured sites |

"Tumor burden" is the sum of the products of the areas (products of maximal perpendicular diameters) of each measurable lesion. As used herein, the tumor burden may either (a) stabilize, which is the failure of the tumor burden to increase, i.e., no new lesions and no increase in the area of any one lesion, or (b) decrease A composition of this invention may be active per se, or may act as a "pro-drug" that is converted in vivo to the active form. The compositions of the invention, as well as the pharmaceutically acceptable salts thereof, may be incorporated into convenient dosage forms, such as capsules, impregnated wafers, tablets or injectable preparations. Solid or liquid pharmaceutically acceptable carriers or excipients are preferably employed. The preparations which can be administered orally or which can be used for other modes of administration, including suitable solutions for administration by injection or infusion, preferably contain from about 0.01% to 15%, preferably from about 0.1% to 10% by weight or by volume of active compound(s), together with the carrier or excipient.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in Gennaro, A E, *Remington: The Science and Practice of Pharmacy*, Lippincott Williams & Wilkins Publishers; 2003 (or a later edition). For human administration, it will be understood that the preparations meet the sterility, pyrogenicity, general safety and purity standards required by FDA Office of Biological Standards and other relevant regulatory bodies.

The pharmaceutical preparations are made using conventional techniques of pharmaceutical chemistry and formulation involving such steps as mixing, granulating and compressing, when necessary for tablet forms, or mixing, filling and dissolving the ingredients, as appropriate, to give the desired products for the various routes of administration described herein including oral and parenteral. The pharmaceutical compositions may contain minor amounts of non-toxic auxiliary substances such as wetting or emulsifying agents, pH buffering agents and so forth.

The present invention may be used in the treatment of any of a number of animal genera and species, and are equally applicable in the practice of human or veterinary medicine. Thus, the pharmaceutical compositions can be used to treat domestic and commercial animals, including birds and more preferably mammals, as well as humans.

Therapeutic compositions or methods for treating tumors and cancer may comprise, in addition to the present composition, one or more additional anti-tumor drugs or agents, such as mitotic inhibitors, e.g., vinblastine; alkylating agents, e.g., cyclophosphamide; folate inhibitors, e.g., methotrexate, antimetabolites, e.g., 5-fluorouracil and cytosine arabinoside, intercalating antibiotics, e.g., adriamycin and bleomycin; enzymes or enzyme inhibitors, e.g., asparaginase, topoisomerase inhibitors such as etoposide; or biological response modifiers, e.g., cytokines and interferons. In fact, pharmaceutical compositions comprising a known cancer therapeutic in combination with the compositions disclosed herein are within the scope of this invention.

The pharmaceutical composition may also comprise one or more other medicaments to treat additional symptoms for which the target patients are at risk, for example, anti-infectives including antibacterial, anti-fungal, anti-parasitic, antiviral, and anti-coccidial agents, since tumor-bearing patients may also suffer from various infections or have diminished resistance to infections.

The present invention provides pharmaceutical combinations or kits which when administered to a subject in need thereof, inhibit cancer cell growth and induce cancer cell death as well as methods of using such combinations to treat many forms of cancer as described. The pharmaceutical compositions of the present invention may, if desired, be presented in a pack or dispenser device which may contain one or more unit dosage forms containing the active compounds. The pack may, for example, comprise metal or plastic foil, such as a blister pack in the case of pills or capsules. The pack or dispenser device may be accompanied by instructions for administration. Compositions comprising a compound of the invention formulated in a compatible pharmaceutical carrier may also be prepared, placed in an appropriate container, and labeled for treatment of an indicated condition. In the present methods, the compounds can also be administered in sustained release forms or from sustained release drug delivery systems. A description of representative sustained release materials can be found in Gennaro, supra.

Having now generally described the invention, the same will be more readily understood through reference to the following examples which are provided by way of illustration, and are not intended to be limiting of the present invention, unless specified.

Example I

Cytotoxic Effect of Magnesium Ascorbate and VK3

The effect of the new Mg-containing formulation, which combined $MgVC_2$+VK3, on proliferation and survival of cancer cells was evaluated was then evaluated using the MTT assay, a calorimetric assay that measures the number of viable cells in a cell sample. 3-[4,5-dimethylthiazol-2-yl]-2,5-diphenyltetrazolium bromide (MTT) is a chromogen that is converted to a measurable colored product by viable cells. Therefore, the amount of color measured is proportional to the number of viable cells. This assay has been used widely to assess the cytotoxicity and selectivity of anti-cancer drugs because MTT is suitable for rapid toxicity characterization of new drug candidates and formulations. One way of assigning a cytotoxic activity to an agent is by converting the raw date to a $CD_{50}$ value, which represent the amount (dose) of the agent needed to achieve 50% of the maximal cytotoxic activity. A lower $CD_{50}$ indicates a greater cytotoxic activity (as a lower amount of the agent is needed to achieve a fixed level of cytotoxicity). Two agents can be compared by examining the fold-increase or decrease in their $CD_{50}$ values.

To evaluate the antitumor activity at a $MgVC_2$:VK3 ratio of 200:1, MgVC was combined with VK3 at a $MgVC_2$:VK3 ratio of 100:1 (which is effectively a VC:VK3 ratio of 200:1). The NaVC:K3 formulation was prepared at a ratio of 200:1.

$MgVC_2$ unexpectedly displayed higher than anticipated efficacy when compared with the equivalent amount of ascorbate provided as NaVC. The antitumor activity of the two formulations against a human androgen-independent prostate cancer cell line DU145 was evaluated in the MTT assay.

The $CD_{50}$ of $MgVC_2$:VK3 was 1.7 to 2.0 fold lower than the $CD_{50}$ of NaVC:VK3, indicating that the former formulation was about twice as potent (Table 5).

With HS68 fibroblast target cells (Table 6), the $CD_{50}$ values of the $MgVC_2$:VK3 were approximately 2.5 to 2.9 times higher than the $CD_{50}$ values of the equivalent $MgC_2$:VK3 formulation for DU 145 tumor cells. This indicates a selectivity for tumor vs. "normal" cells.

TABLE 5

Cytotoxicity of the Vitamins and Vitamin Combinations Treating DU145 Prostate Cancer Cells

| | Vitamin Combinations | | | | | | | | | |
|---|---|---|---|---|---|---|---|---|---|---|
| | Vitamins Alone | | | Vitamin C:Vitamin K3 100:1 | | | | Vitamin C:Vitamin K3 200:1 | | Magnesium C |
| | | | | NaVC | | $MgVC_2$ | | Sodium C | | |
| Time in Days | NaVC $CD_{50}$ (μM) | $MgVC_2$ $CD_{50}$ (μM) | VK3 $CD_{50}$ (μM) | VC $CD_{50}$ (μM) | VK3 $CD_{50}$ (μM) | VC $CD_{50}$ (μM) | VK3 $CD_{50}$ (μM) | VC $CD_{50}$ (μM) | VK3 $CD_{50}$ (μM) | VC $CD_{50}$ (μM) | VK3 $CD_{50}$ (μM) |
| 1 | 3068 | 2508 | 37.5 | 473 | 4.7 | 154 | 1.5 | 328 | 1.6 | 206 | 1.0 |
| 2 | 1484 | 1146 | 37.5 | 469 | 4.7 | 134 | 1.3 | 235 | 1.2 | 196 | 1.0 |
| 3 | 994 | 432 | 37.5 | 456 | 4.7 | 132 | 1.3 | 234 | 1.2 | 172 | 0.9 |

TABLE 6

Cytotoxicity of the Vitamins and Vitamin Combinations Treating HS68 Fibroblasts

| | Vitamins Alone | | | Vitamin Combinations | | | | | | |
|---|---|---|---|---|---|---|---|---|---|---|
| | | | | Vitamin C:Vitamin K3 100:1 | | | | Vitamin C:Vitamin K3 200:1 | | |
| | | | | NaVC | | MgVC$_2$ | | NaVC | | MgVC$_2$ |
| Time in Days | NaVC CD$_{50}$ (μM) | MgVC$_2$ CD$_{50}$ (μM) | VK3 CD$_{50}$ (μM) | VC CD$_{50}$ (μM) | VK3 CD$_{50}$ (μM) | VC CD$_{50}$ (μM) | VK3 CD$_{50}$ (μM) | VC CD$_{50}$ (μM) | VK3 CD$_{50}$ (μM) | VC CD$_{50}$ (μM) | VK3 CD$_{50}$ (μM) |
| 1 | 1468 | 1663 | 18.7 | 458 | 4.7 | 382 | 3.8 | 466 | 2.3 | 392 | 3.8 |
| 2 | 1245 | 1746 | 19.0 | 471 | 4.7 | 383 | 3.8 | 467 | 2.3 | 348 | 1.7 |
| 3 | 1185 | 1501 | 18.7 | 471 | 4.7 | 342 | 3.4 | 397 | 2.0 | 193 | 1.0 |

Example II

Induction of DNase I and DNase II by MgVC$_2$ and VK3

Because endonuclease activation is one of the earliest changes denoting irreversible commitment to cell death, it is generally believed to be involved in the triggering, rather than being merely a result of, cell. DNase I and DNase II and their fate are of particular interest because (a) these enzymes are broadly distributed in normal tissues and (b) they have been implicated as possible effectors of cell death (Peitsch M C et al. (1994) *Trends Cell Biol* 4:37-41; Krieser R J et al. (1998) *J Biol Chem* 273:30909-14)

DNase I has an alkaline pH optimum of about 7.5. For optimal enzymatic activity, DNase I requires either μM concentrations of both Ca$^{2+}$ and Mg$^{2+}$ or 1 mM Mg$^{2+}$ alone. DNase I is localized primarily in the mitochondria, though activity is also detectable in the nucleus (Beaufay, H. et al., 1959, *Biochem J.* 73:623-8) especially in the endoplasmic reticulum/nuclear envelope (Peitsch et al. 1993, *EMBO J.* 12:371-7). DNase I activity is latent in tumor cells and can be rapidly re-expressed, for example, within 15 min of exposure to VK3 which results in release from the enzyme's inhibitor.

DNase II does not require divalent cations for its activity and has an acidic pH optimum of about 5.0 (Allfrey V et al., 1952, *J Gen Physiol* 36:227-241; Peitsch et al., 1994, supra). Although the specific activity of DNase II is highest in lysosomes, over 50% of the total cellular DNase II is found in the nuclear fraction. DNase II activity is also latent in tumor cells, but can be re-expressed, for example, by exposure to Vitamin C within in about 4 h in vivo and about 1 h in vitro, as a result of release of DNase II from its inhibitor.

Detection of DNase I

Poly-L-lysine (PLL)-coated coverslips were seeded with 10$^5$ tumor cells or normal human foreskin fibroblasts and incubated overnight at 37° C. in an atmosphere of 5% CO$_2$ to allow cells to attach and spread. The cells were washed once with medium and then sham-treated or incubated for 15 minutes with one or more of the following agents or combinations:

TABLE 7

| | Concentration of agents (μM) | | |
|---|---|---|---|
| Group | Vitamin C (VC) | Mg Vitamin C (MgVC$_2$) | Vitamin K3 (VK3) |
| 1 | 250 | — | — |
| 2 | — | 250 | — |
| 3 | — | 125 | — |
| 4 | — | — | 5 |
| 5 | 125 | | 1.25 |
| 6 | — | 125 | 1.25 |
| 7 | — | 250 | 2.5 |

Subsequently, the vitamin-containing (or control) medium was decanted, and the cells were washed thrice in phosphate-buffered saline (PBS). The cells were then fixed at room temperature for 10 min in 3.7% formaldehyde/PBS, washed thrice in PBS and permeabilized for 5 min at −20° C. with acetone. Cells were air dried for 5 min, washed thrice in PBS and incubated with a 1:500 dilution of an alexa-fluor 488-conjugated human DNase I (Invitrogen). The cells were then washed thrice in PBS. The last PBS wash contained the fluorescent nuclear stain 4',6-diamidino-2-phenylindole (DAPI) which was used to stain nuclei. The cell-bearing coverslips were mounted on slides using 50% glycerol/PBS. Auto-fluorescence was controlled using the following two treatments: (a) sham-treated cells incubated with antibody and (b) cells treated as with Group 6, above, but with omission of the alexa-fluor DNase I conjugate.

DNase II Immunocytochemistry

PLL-coated coverslips were seeded with cells as above. The cells were washed once with medium and then sham-treated, or treated for 1 hour with one or more of the following agents or combinations:

TABLE 8

| | Concentration of agents (μM) | | |
|---|---|---|---|
| Group | Vitamin C (VC) | Mg-Vitamin C (MgVC$_2$) | Vitamin K3 (VK3) |
| 1 | 250 | — | — |
| 2 | — | 125 | — |
| 3 | — | — | 2.5 |
| 4 | 125 | | 1.25 |
| 5 | — | 62.5 | 1.25 |

After decanting the vitamin-containing medium, cells were washed, fixed and permeabilized as above. Cells were air dried for 5 min and then washed thrice in PBS and incubated with a 1:1000 dilution of a polyclonal rabbit anti-human antibody to the C-terminus (amino acids 347-360) of DNase II (Chemicon International). The cells were then washed thrice in PBS and incubated for 1 hr at room temperature with a 1:1000 dilution of secondary antibody, goat anti-rabbit IgG, to which was conjugated alexa-fluor 688 (Invitrogen). Cells were next washed 5× with PBS, rinsed with distilled water and air dried for 5 minutes. The nuclei were stained with DAPI and the coverslips mounted as above. Auto-fluorescence and antibody specificity were monitored and controlled for using (a) sham-treated cells or (b) cells treated as in Group 4, above, but without omission of the primary (anti-DNase II) antibody.

Results

Previous studies by the present inventors and their colleagues showed that tumor cells treated with the combination of VC:VK3 were specifically killed by a mechanism known as autoschizis. Because endonuclease activation is one of the earliest changes denoting irreversible commitment to cell death, it is generally accepted as triggering cell death rather than being a mere consequence of cell death.

After 15 minutes exposure to NaC/VK3 (FIG. 1A), DNase I was localized primarily as a circumferential perinuclear band. This band most likely indicated DNase I localization in the endoplasmic reticulum/nuclear envelope. DAPI staining (FIG. 3A) indicated that chromatin was unaffected which suggested that the DNase I was inactive.

Conversely, following a 15 minute exposure to $MgVC_2$/VK3 (FIG. 1B), DNase I was evenly distributed across the nucleus. DAPI staining (FIG. 3B) revealed the presence of islands of condensed chromatin which suggested that the DNase I was active.

No change in localization of DNase II was observed following 15 minute exposure to either $NaVC/VK^3$ or $MgVC_2/VK^3$ (not shown). However, following a 1 h exposure to NaVC/VK3 (FIG. 2A), immunolocalization revealed that DNase II was localized primarily in punctate islands within the nucleus and as discrete bodies in the cytoplasm. DAPI staining (FIG. 3A) indicated homogenous staining of the chromatin which suggested that the DNase II was inactive.

Conversely, following 1 h exposure to $MgVC_2$/VK3 (FIG. 2B), immunolocalization revealed diffuse DNase II staining across most of the nucleus with intense staining of the chromatin along one pole. Likewise, the DNase II staining in the cytoplasm had become more diffuse. The time course of the development of this diffuse cytoplasmic staining is in agreement with the results of other studies demonstrating the development of permeabilized lysosomes (not shown). Finally, DAPI staining (FIG. 3B) indicated a pronounced margination of the chromatin which suggested that the DNase II was active.

Example III

Formulations

A. Capsules

The preferred embodiment of the method utilizes oral delivery. Capsules of a combination of $MgVC_2$/VK3 are prepared with the agents in a predetermined ratio. For example, 0.5 g of Mg ascorbate (L-Ascorbic acid magnesium salt) is combined with 0.005 g of water soluble vitamin K3 (menadione sodium bisulfite). Both vitamins are mixed in the powdered form and placed in capsules without supplementary ingredients at the predetermined ratio such as is 100:1.

B. I.V. Formulations

For i.v. delivery solutions of L-Ascorbic acid magnesium salt and vitamin K3 are prepared and stored separately and mixed directly before intravenous infusion. Exemplary i.v. solutions are prepared as follows:

$MgVC_2$: 5 g Magnesium ascorbate; 1.2 g NaCl; 300 ml Sterile, apyrogenic water for injection.

Vitamin K 50 mg Menadione sodium bisulfite; 5 ml Sterile, apyrogenic water for injection.

These solutions should be oxygen-free (e.g. perfused with gaseous nitrogen); sterilized by filtration (such as by filtration through filters of pore diameter of about 0.22 μm or lower); and introduced into sterile, oxygen-free, packets for the vitamin C solution or glass vials for vitamin K3 solution. Each series of prepared pockets or vials must be examined for pyrogenicity and sterility by standard methods. Since both vitamins are sensitive to oxygen, light, and temperature, the solutions should be stored in under anoxic conditions at approximately 4° C. in the dark to insure their effectiveness.

The intravenous solution is also prepared by mixing 5 grams of Vitamin C and 50 mg of Vitamin K3 in 300 ml of sterile non-pyrogenic normal saline in an i.v. bag immediately prior to use.

Example IV

Treatment of Cancer Patients

Patients with a variety of types of cancer are treated as described below with oral administration of $MgVC_2$/VK3.

Dosing: Orally (capsules) 4 capsules per day at 5 hr intervals

Dose per capsule of $MgVC_2$: 1 g-5 gm

Dose per capsule of VK3m: 10 mg-50 mg

Duration: Initiated at day 0 and continues for up to 90 days

Patient Evaluation

Assessment of response of the tumor to the therapy is made once per week during therapy and 30 days thereafter. Depending on the response to treatment, side effects, and the health status of the patient, treatment is terminated or prolonged from the standard protocol described herein. Tumor response criteria are those established by the International Union Against Cancer and are listed in Table 2 above.

The efficacy of the therapy in a population is evaluated using conventional statistical methods including, for example, the Chi Square test or Fisher's exact test. Long-term changes in and short term changes in measurements can be evaluated separately.

Results 240 patients with types of cancer indicated in Table 9 are treated. The results are summarized in Table 9. Positive tumor responses (including CR, PR and <PR, are observed in about 70% of the patients as follows. Eight patients have complete responses:

TABLE 9

| All Patients | | |
|---|---|---|
| RESPONSE | n | % |
| CR | 8 | 3.3 |
| PR | 108 | 45 |
| <PR | 53 | 22 |

| TUMOR TYPES | n | RESPONSE | % OF patients |
|---|---|---|---|
| Breast Adenocarcinoma | 30 | PR + <PR | 75% |
| Gastrointestinal Carcinoma | 30 | PR + <PR | 68% |

TABLE 9-continued

| All Patients | | | |
|---|---|---|---|
| Lung Carcinoma | 30 | PR + <PR | 57% |
| Prostate Carcinoma | 30 | PR + <PR | 68% |
| Lymphoma/Leukemia | 30 | PR + <PR | 75% |
| Head and Neck Cancer | 30 | PR + <PR | 60% |
| Renal and Bladder Cancer | 30 | PR + <PR | 66% |
| Ovarian Cancer | 30 | PR + <PR | 72% |

Side Effects:

Virtually no toxicity is observed. Small numbers of patients (<1% of total) show signs that can not be attributed to the drug combination, such as fatigue, pain, nausea, headache, hypertension, diarrhea, itching, and dizziness. Toxic effects usually associated with systemically administered chemotherapeutic agents are not observed.

Conclusion:

MgVC$_2$/VK3 at the doses used is an effective anti-cancer drug against a wide range of cancer types.

Example V

Patient Monitoring by Measuring Serum Alkaline DNase

The effectiveness of the treatment according to the invention can also be monitored in individual patients using a method based on the variations of serum alkaline DNase activity ("SADA"). The suitability of this test for cancer therapy prediction and post-therapeutic monitoring is based on histochemical observations that this DNase was deficient in non-necrotic cancer cells and was reactivated in early states of necrosis (both spontaneous and induced by treatment). Due to the great inter-individual differences of SADA between cancer patients before treatment, as well as due to the lack of distinct differences in SADA levels between cancer patents and normals, this assay is not useful for cancer detection. However, multiple measurements of SADA in cancer patients during and after the treatment is a useful and valuable means for prognosis and post-therapeutic monitoring.

SADA variations have been investigated and compared to the clinical evolution of cancer in more than 600 patients with lymphomas; bronchogenic carcinomas, nonlymphoblastic leukemias, upper respiratory tract cancers, head and neck cancers and in various types of cancers. The results in human patients were confirmed in tumor-bearing rats. SADA variations were also investigated in normal humans.

Preferably, the SADA measurements are obtained using the following procedures:

(1) Temperature of incubation: 50° C.
(2) Time and incubation: 60 minutes.
(3) Volume of tested serum: 100 μl. in 900 μl of Tris buffer at pH 8 with substrate 500 μg DNA substrate (sodium salt, from calf thymus).
(4) The presence of CaCl$_2$ and MgCl$_2$ in the incubation medium.
(5) Precipitation procedure: done in ice bath by adding saturated MgSO$_4$.7H$_2$O solution and vortexing, addition of 25N PCA, vortexing, 20 min.; centrifugation at 2000 g.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

What is claimed is:

1. A composition useful for of killing or inhibiting the growth of tumor or cancer cells or for treating cancer in a subject in need thereof, which composition comprises a combination of magnesium ascorbate (MgVC$_2$) and Vitamin K3 (VK3) wherein the ratio of MgVC$_2$ to VK3 is from 50:1 to 500:1.

2. The composition of claim 1 wherein the ratio of MgVC$_2$ to VK3 is from 100:1 to 200:1.

3. The composition of claim 1 wherein said VK3 is 2-methyl-1,4-naphthoquinone sodium bisulfite.

4. A pharmaceutical composition comprising:
(a) the composition of claim 1; and
(b) a pharmaceutically acceptable carrier or excipient.

5. The pharmaceutical composition of claim 4 that is formulated as a capsule for oral administration.

6. A kit comprising a plurality of capsules according to claim 5, and, optionally, directions for use of the capsules.

7. A method of killing or inhibiting the growth of tumor or cancer cells in a subject in need thereof, comprising administering to said subject the composition of claim 1 in an amount effective to kill or inhibit the growth of said tumor or cancer cells.

8. The method of claim 7 wherein the ratio of MgVC$_2$ to VK3 is from 100:1 to 200:1.

9. The method of claim 7 wherein the amount of MgVC$_2$ administered to the subject per day is between 15 mg and 1 gram per kg body weight, and the amount of VK3 administered per day is between 30 μg and 20 mg per kg body weight.

10. The method of claim 7 wherein said VK3 is 2-methyl-1,4-naphthoquinone sodium bisulfite.

11. The method of claim 7 wherein the administering is oral, intravenous, intranasal or intraperitoneal.

12. The method of claim 7 wherein the tumor or cancer cells being killed or inhibited are breast cancer cells, colon cancer cells, prostate cancer cells, lymphoma cells, leukemia cells, lung cancer cells, head or neck cancer cells, brain tumor cells, ovarian cancer cells or liver cancer cells.

13. A method for treating cancer in a subject in need of such treatment, comprising administering to said subject an effective amount of a composition according to claim 1, in an amount effective to kill or inhibit the growth of said tumor or cancer cells.

14. The method of claim 13 wherein the tumor or cancer being treated is breast cancer, colon cancer, prostate cancer, lymphoma, leukemia, lung cancer, head or neck cancer, a brain tumor, ovarian cancer or liver cancer.

* * * * *